United States Patent [19]

Reuning et al.

[11] Patent Number: 4,764,601
[45] Date of Patent: Aug. 16, 1988

[54] COMPOSITION FOR ASSAYING CARDIAC GLYCOSIDES FROM SERUM OR PLASMA

[75] Inventors: Richard H. Reuning; James Hui, both of Columbus, Ohio; Theresa A. Shepard, Shillington, England; Richard A. Sams, Columbus, Ohio

[73] Assignee: The Ohio State University Research Foundation, Columbus, Ohio

[21] Appl. No.: 788,822

[22] Filed: Oct. 18, 1985

[51] Int. Cl.[4] .................. A61K 31/70; C07J 19/00
[52] U.S. Cl. .................................. 536/5; 436/93; 436/94; 436/131; 436/172; 436/174; 436/161; 422/70; 210/198.2; 73/61.1 C; 514/26
[58] Field of Search .......................... 536/5; 514/26

[56] References Cited

U.S. PATENT DOCUMENTS 4,184,037  1/1980  Wilkinson ........................ 536/5
4,555,504  11/1985  Jones ............................... 536/5

FOREIGN PATENT DOCUMENTS 484578  7/1952  Canada ............................. 536/5
488775  12/1952  Canada ............................. 536/5

OTHER PUBLICATIONS

Abstract Assay of Digoxin and Metabolites in Urine and Feces by HPLC of Fluorescent Derivatives, Theresa Shepard and Richard H. Reuning, College of Pharmacy, OSU, Columbus, OH 43210, p. 647, World Conference on Clinical Pharmocology Therapeutics, Washington, D.C., Jul. 31–Aug. 5, 1983.
I. Methods for Digoxin and Metabolite Determination in Urine, Feces and Plasma and Application to Detection of R-Dihydrodigoxin in Humans and II. A Theroretical Examination of the Kinetics of Enterohepatic Cycling, by Theresa A. Shepard, Ph.D. The Ohio State University, 1983 Professor Richard H. Reuning, Advisor.

*Primary Examiner*—Ronald W. Griffin
*Attorney, Agent, or Firm*—Sidney W. Millard

[57] ABSTRACT

A fluorescent compound is made from the reaction of naphthoyl chloride and a cardiac glycoside derived from serum or plasma. The method of carrying out the reaction provides a product which allows for a 100-fold increase in sensitivity when the product is subjected to chromatographic analysis according to the described apparatus.

6 Claims, No Drawings

COMPOSITION FOR ASSAYING CARDIAC GLYCOSIDES FROM SERUM OR PLASMA

The invention was made with U.S. government support under grant number 5 R01 AG04119-02 awarded by the National Institute of Aging. The government has certain rights in the invention.

FIELD OF THE INVENTION

This invention relates to assays for cardiac glycosides for monitoring the serum or plasma cardiac glycosides concentration of patients taking cardiac glycosides.

BACKGROUND OF THE INVENTION

Assays for digoxin that have been commercially marketed all involve immunoassay technology. These immunoassays are used routinely in hospital clinical laboratories to monitor the serum digoxin concentration of patients taking digoxin. The strength of these immunoassays is their impressive sensitivity (about 0.1 ng/ml lower limit; the "therapeutic range" in patients is 0.5–2.0 ng/ml serum) and their ease of performance in a clinical laboratory. The important limitation is that the immonoassay does not measure only digoxin; it also measures interfering active and inactive metabolites of this drug, as well as endogenous interfering substances currently referred to as digitalis-like immunoreactive substances (DLIS).

Some investigators have combined high performance liquid chromatography (HPLC) with immunoassay in order to separate metabolites by HPLC and then detect them by immunoassay. The limitation of this technique is that some metabolites are not detected by immunoassay techniques. Others have combined HPLC with radioactivity detection. the limitation of the latter technique is that radioactive drug must be administered and therefore the method is not applicable in the normal setting of clinical use.

Digoxin and digitoxin are the two digitalis cardiac glycosides that are used most frequently in a clinical setting. Digoxin is used much more frequently than digitoxin and has been the subject of extensive scientific investigation, including investigations aimed at developing analytical methodology. For convenience, the assay techniques will be outlined.

Radioimmunoassay

Since the early 1970's there have been a variety of methodological improvements in radioimmunoassay (RIA) and it has been commercialized with numerous suppliers currently available. Digoxin in a serum sample competes with a radiolabeled digoxin tracer (or digoxin derivative) for binding sites on the antibody to digoxin. The unbound digoxin (both labeled and unlabeled) is then separated from the bound digoxin-antibody complex, and the bound or unbound radiolabeled digoxin is quantitated. The concentration of unlabeled digoxin in the serum sample is calculated by comparison to digoxin standards. Some RIA procedures utilize $^3$H-digoxin as the tracer (liquid scintillation quantitation) while others use a digoxin derivative labeled with $I^{125}$ (gamma counter quantitation).

The RIA has become the most popular method of digoxin analysis, both for clinical therapeutic drug monitoring and for scientific purposes, because of its ease of performance, its sensitivity and its precision. The sensitivity of most current RIA kits is 0.2–0.4 ng/ml of serum (below the therapeutic range) and it has been reported that a modified procedure sensitive to 0.05 ng/ml is available. The coefficient of variation for repetitive determinations is in the range of 5–15% at therapeutic concentrations for several different RIA kits and is dependent on the method of data analysis.

Despite the reported precision of the digoxin RIA there are potential problems in the inter-patient reproducibility of RIA results that were reported as early as 1972. One specific factor that can influence the RIA with liquid scintillation counting of $^3$H-digoxin is the elevation of apparent digoxin concentration due to quenching from hemolysis products in the serum or plasma or quenching from hyperbilirubinemic plasma. This problem was only partially resolved with a quench-correction curve and has led to a preference for the digoxin derivative containing the gamma-emitting $^{131}$I isotope. Albumin concentration has been shown to influence the results of the $^{131}$I technique, with a hypoalbuminemic serum sample yielding a falsely lowered serum digoxin concentration. In addition, others have reported that tracer binding to the antibody is increased when the usual $^{131}$I-digoxi derivative (3-0-succinyl-digoxigenin-{$^{125}$I}-tyrosine) is used with sera having a low thyroxine concentration. This results in a falsely lowered apparent digoxin concentration. Quantitation of both the beta-emitting $^3$H-digoxin and the gamma-emitting $^{131}$I-digoxin derivative in serum is influenced by the presence of gamma-emitting radioisotopes from various diagnostic tests.

Drug-related substances also have the potential to interfere with the RIA for digoxin, but this appears to be manageable. Interference by concurrent therapy with spironolactone may be a problem in sera from certain patients, but the extent of this problem is not clear and is dependent on the type of RIA procedure used. When Fab fragments of digoxin-specific antibodies are used to treat digoxin intoxication, the Fab fragment interferes with the digoxin RIA. Again the interference varies from one RIA kit to another. Other cardiac glycosides may also react with the antibody in the digoxin RIA, usually to a relatively small extent. However, cross reactivity with digitoxin can be clinically significant.

Lack of specificity of the digoxin RIA with respect to both active and inactive metabolites has been reported for certain RIA kits. The pharmacologically active, sugar-hydrolyzed metabolites digoxigenin bisdigitoxoside and digoxigenin monodigitoxoside were essentially equal to digoxin in RIA cross-reactivity. The less potent digoxigenin was much less cross-reactive in the RIA. This similarity in pharmacologic potency and RIA cross-reactivity is viewed by some as a fortunate coincidence that permits clinical use of the RIA to measure a serum concentration that is a reflection of total digitalis-like activity. However, it should be cautioned that even the degree of cross-reactivity of these metabolites varied widely in a comparative study of six commercial RIA procedures. Of potentially greater clinical significance is the cross-reactivity between the relatively inactive dihydrodigoxin and the digoxin antibody. This was originally demonstrated with one commercial source and was then shown to vary from negligible to substantial (about 30% in the therapeutic range) in four different $^{125}$I-RIA kits. In a recent survey of six different commercial $^{125}$I-RIA kits, the greatest cross reactivity for dihydrodigoxin was about 11%, a value judged to be insignificant clinically. One unanswered question with respect to assay specificity is whether potentially interfering metabolites are actually present in serum. This would be most likely to occur in renal disease where the possibility of reduced excretion of metabolites is greatest, or in gastrointestinal diseases that lead to intestinal bacterial overgrowth, where the possibility of increased formation of inactive dihydro metabolites is greatest. Bacterial overgrowth of the upper intestine is as yet uninvestigated with respect to digoxin metabolism and serum concentrations. However, some researchers have combined RIA with prior separation of digoxin and hydrolyzed metabolites in order to determine that 6–42% of radio-immunoassayed serum digoxi may represent compounds other than digoxin. Others have also compared RIA versus RIA with prior HPLC separation for analysis of serum digoxi in children and found that prior separation resulted in serum concentrations that averaged 64% of radioimmunoassayed serum concentrations. Evidence currently suggests the presence of either metabolites or an interfering substance in serum from renal failure patients and in serum from children, but not in serum from normal adults. Recent reports of an immunoreactive endogenous digitalis-like substance in patients with renal failure and in neonates and infants are pertinent but analysis is unnecessary for an understanding of the inventive concepts hereinafter disclosed.

The preceding summary pertaining to the digoxin RIA yields a confusing and sometimes contradictory picture of the important factors that influence RIA results. The major reason for this is that the procedures, and especially the antibodies, are not the same for kits from different manufacturers. Despite these limitations, RIA has proven to be very helpful in management of patients requiring digoxin. For the $^{131}$I-RIA kits, one must be alert for spironolactone administration, diagnostic radioisotopes, hypoalbuminemia and hypothyroidism that may influence assay results. In addition, information from individual manufacturers regarding cross-reactivity with endogenous substances in serum and with known digoxi metabolites (and preferably lot-to-lot variability in cross-reactivity) must be available for intelligent interpretation of RIA results, particularly in patients with renal failure, and in children.

Enzyme Immunoassay

Enzyme immunoassays are a more recent development than RIA and are closely related. In this technique, digoxin-enzyme (digoxin chemically bonded to an enzyme) competes with serum digoxin for digoxin-antibody binding sites. Depending on the particular procedure, either free or antibody-bound digoxi-enzyme is then reacted with an excess substrate for the enzyme, together with cofactors. The enzyme reaction produces a UV chromophore which is measured spectrophotometrically. The precision and sensitivity of the enzyme immunoassay are similar to RIA.

Because enzyme immunoassays depend on competition for an antibody binding site, they suffer from most of the same disadvantages as RIA. Interference from non-specific plasma components and from spironolactone administration are both suspected. Essentially complete cross-reactivity with the active, hydrolyzed metabolites of digoxi has been demonstrated for one commercial antibody whereas the inactive dihydrodigoxin did not cross-react.

Enzyme immunoassays do not suffer from disadvantages related to radioactivity measurement. One distinct advantage of these more recent procedures is the quantitation of a UV chromophore which is technically easier and requires less investment in equipment.

Fluorescence Polarization Immunoassay

Another recent addition to the array of immunoassays for digoxin is the fluorescence polarization immunoassay. The method is based on the ability of a fluorescein-labeled digoxin tracer to compete with unlabeled serum digoxi for antibody binding sites. Upon excitation by single-wavelength, polarized light, the unbound label and antibody-bound fluorescent label exhibit widely different degrees of polarization of emission fluorescence, upon which quantitation is based. This method has excellent reproducibility with a coefficient of variation of <6% for inter-day replicates. Data provided by the manufacturer indicates a high degree of cross-reactivity for all of the hydrolyzed metabolites, including the less active digoxigenin. Little cross-reactivity was found for dihydrodigoxin and digitoxin. The endogenous digitalis-like immunoreactive substance found in neonates and infants interferes with the fluorescence polarization immunoassay in some patients.

Chromatographic Methods

Chromatographic analytical methods offer potentially greater specificity with respect to interference from metabolites and endogenous plasma constituents than do immunological methods. However, the usual means of detection in chromatography do not permit analysis at serum concentrations due to the general lack of detectable functional groups on the digoxin molecule. Thus, the only chromatographic methods that have been applied to analysis of serum samples have utilized tritiated digoxin administration coupled with liquid scintillation counting of separated fractions or have coupled chromatographic separation with RIA. Such methods are labor-intensive, and are not feasible for routine clinical use, but offer the advantage of assaying metabolites as well as unchanged digoxin and of analyzing these substances in urine and tissues as well as in serum. Another approach that potentially offers both specificity and adequate sensitivity, is the combining of chemical derivatization of digoxin and metabolites with chromatographic separation. Such a technique using a UV-absorbing derivative, has proven adequate for analysis of digoxi, its three hydrolyzed metabolites and dihydrodigoxin in urine. Fluorescent derivatives or use of microbore HPLC technology with UV-absorbing derivatives offer the potential for subnanogram sensitivity, which is necessary for analysis of serum concentrations of digoxin and its metabolites. Although chromatographic analysis is not currently feasible for routine therapeutic drug monitoring because of limited sensitivity, difficulty of performance, and long turnaround time, it is an important evolving technique for investigations of digoxin metabolism and pharmacokinetics.

The fluorescent ester approach has been applied to the development of an analytical method for digoxi and its major metabolites in urine and feces. The sensitivity limit was 25 ng in 1.0 ml urine and 10 ng in 200 mg feces. Assays for digoxin and metabolites in serum must be at least 50–100 fold more sensitive in order to compete with immunoassays (sensitivity limit 0.1–0.2 ng/ml) and cover the therapeutic range of 0.5–2.0 ng/ml (as determined by immunoassay).

SUMMARY OF THE INVENTION

In this invention a serum or plasma sample first has digitoxin added in a specific amount to give a known amount of digitoxin in the sample. Thereby, when resulting sample is analyzed by chromatography, the peaks on the chart will allow a ratio comparison of the known digitoxin with the other peak to indicate the concentration of digoxin in serum by a ratio comparison.

The sample is then dried by a known vacuum method and washed with a dilute base, water and other dilute acids and solvents to remove impurities, and the resulting product is reduced to solid form by evaporation. It is then treated with a fluorescent chloride, caused to react by a suitable catalyst, mixed vigorously and heated to a suitable temperature and allowed to react. Thereafter the liquids are removed, the product washed and the product again dried. It is then mixed with a mixture of hexane, methylene chloride and acetonitrile and fed through an analytical column in a chromatography system and the graph subsequently analyzed.

Thus, the main achievement of the current methodology for serum is greater than 100-fold increase in sensitivity over that previously reported for digoxin and its metabolites in urine. This was at least partially achieved by means of the following improvements: (1) replacement of the liquid-liquid extraction technique with a solid-phase extraction, thus permitting substantially improved clean-up of the serum extract and removing blank interferences from serum; (2) reduction of the dilution due to dead volume in the HPLC system by optimizing the HPLC plumbing for minimal dead volume, (3) reduction of the amounts of derivatizing agent (naphthoyl chloride) and catalyst (dimethylaminopyridine, DMAP) yielding less blank interference yet complete derivatization, (4) use of shorter HPLC columns packed with smaller particle size silica, (5) use of a new injector valve with zero dead volume, (6) use of naphthoyl chloride that has been purified by fractional distillation.

DESCRIPTION OF THE PREFERRED EMBODIMENT

In the specific procedures used as will be described subsequently, apparatus from J. T. Baker Chemical Company identified by the trademark "Baker-10 SPE" was used and specifically where we refer to "columns" we are referring to specifically identified columns supplied by J. T. Baker Chemical Company and their use, size, incorporated chemicals, etc. are known in the industry, and will not be described herein. For example, in the columns referred to below we can use any of the Baker-10 SPE columns of six ml capacity identified as C18, C=N, C8 and phenyl.

First the column volume is cleansed by passing a column volume of methanol, a column volume of acetonitrile and three columns of double distilled demineralized water to remove as many of the impurities from the column as possible before the addition of the plasma or serum sample.

Next a 2 ml sample of serum is supplied and from one to ten nanograms of digitoxin is added. Then the sample is applied to the column and a vacuum is drawn on the column for four minutes by a standard Baker vacuum system, which is known in the industry, and the vacuum is drawn by hooking the system to a standard spigot connected to tap water and the system draws about fifteen inches of mercury vacuum.

Two column volumes of 5% $NaHCO_3$ and three column volumes of distilled water are then fed through the column and the vacuum is then applied for four minutes. A 20% solution of acetone in water, methanol and other similar washing solvents may be substituted for the 5% solution of $NaHCO_3$ where mentioned subsequently. Acetonitrile (1-2 ml) is used to elute the compounds into a test tube and the acetonitrile is then evaporated by a standard system at 55° C. under nitrogen gas for about ten minutes until the acetonitrile is completely evaporated.

The dry residue is then treated with 2 ml of chloroform and with 2 ml of the 5% solution of $NaHCO_3$. Methylene chloride may be substituted for chloroform where mentioned in this description. This is followed by vigorous mixing, centrifuging and a discarding of the aqueous solution. The chloroform is then treated with 2 ml of 0.05 N HCl followed by vigorous mixing centrifuging and discarding of the aqueous solution and an evaporation of the chloroform.

Where the description of the process refers to solutions of $NaHCO_3$, numerous other weak bases may be used as a substitute. Similar comments are applicable to weak concentrations of acids where a 0.05 normal solution of hydrochloric acid is used.

The next procedural step involves the derivatization and it basically involves the step of treating the solid residue from the above procedure with a fluorescent chloride so as to cause the fluorescent chloride to attach to the molecules to be identified in this procedure. The preferred chloride is 1-naphthoyl chloride. A 1 $\mu l$ sample is required and it is prepared by using a 20 $\mu l$ of a 10 $\mu l$/200 $\mu l$ solution in acetonitrile. A catalyst is required to make the fluorescent chloride attach to cardiac glycosides and various catalysts can be used.

In the particular experiments conducted, a 2.5 mg dimethylaminopyridine catalyst was used and it was prepared with 100 $\mu l$ of a 25 mg per ml solution in acetonitrile; a further 250 $\mu l$ acetonitrile was then added. The product was then vigorously mixed for thirty seconds and heated in a water bath to about 50° C. for 2 hours to allow the reaction to occur.

The naphthoyl derivative of digitoxin has a different chromatographic retention time than that of digoxin.

The product was then centrifuged and the acetonitrile evaporated. This was followed by cleansing steps involving the addition of, in sequence, 2 ml of a dilute base and a mixing for five minutes; 2 ml of chloroform with vigorous mixing, centrifuge and removal of the aqueous solution; 2 ml of a weak base followed by mixing, centrifuging and removing of the aqueous solution; 2 sequential steps of adding 2 ml of a weak acid, shaking, centrifuging and removing the aqueous solution, and finally the chloroform is evaporated. The product is now ready for the chromatograph.

In the procedure used, the sample was reconstituted with about 150 $\mu l$ of a mixture called the "mobile phase" which consists of a mixture of hexane, methylene chloride and acetonitrile approximately in the ratios of 27:5:5. The product and mobile phase was then loaded with a 2×loop volume (40 $\mu l$) and injected into an analytical column of a very specific nature. The product was supplied by All Tech Associates, Inc. and was 150 mm in length by 4.6 mm inside diameter and contained 3 $\mu m$ silica. The mobile phase was then pumped through the analytical column at 1.4 ml per minute with a total analysis time of about ten minutes.

The specific pieces of apparatus used in addition to the analytical column are as follows;

- Guard Column: 15 mm L×3.2 mm ID, 7 μm Silica (Brownlee Labs)
- Pump: Model 2010 HPLC Pump (Varian Instruments Group)
- Injector: Model 3XL HPLC Injector with 20 μl external loop (Scientific Systems, Inc.)
- Detector: Model FS970 Spectrofluoro Monitor (Kratos Analytical Instruments) Flow cell size: 5 μl
- Recorder: Omniscribe Recorder (Houston Instruments).

We claim:

1. A composition consisting essentially of: (i) a first fluorescent compound which includes a moiety of a cardiac glycoside from one of serum and plasma derivatized by a naphthoyl moiety from a naphthoyl chloride purified by fractional distillation; (ii) a second and different flourescent compound which includes a moiety of a known cardiac glycoside derivatized by a naphthoyl moiety from said naphthoyl chloride purified by fractional distillation; and (iii) a liquid mobile phase for said first and second compounds.

2. The composition of claim 1 in which the liquid mobile phase consists essentially of hexane, methylene chloride and acetonitrile.

3. The composition of claim 2 wherein the hexane, methylene chloride and acetonitrile are present in a ratio of about 27:5:5.

4. The composition of claim 1 in which digoxin is said cardiac glycoside from one of serum or plasma.

5. The composition of claim 1 in which said cardiac glycoside from one of serum or plasma is digoxin and in which said known cardiac glycoside is digitoxin.

6. The composition of claim 5 in which said naphthoyl chloride purified by fractional distillation is 1-naphthoyl chloride.

* * * * *